United States Patent [19]

Fluent et al.

[11] 4,223,674
[45] Sep. 23, 1980

[54] IMPLANT GUN

[75] Inventors: Stewart L. Fluent, Cedar Falls, Iowa; Dan R. Foley, LaVerne, Calif.

[73] Assignee: Arthur J. McIntosh, Waverly, Iowa

[21] Appl. No.: 920,381

[22] Filed: Jun. 29, 1978

[51] Int. Cl.³ .............................................. A61M 5/18
[52] U.S. Cl. ................................................... 128/217
[58] Field of Search ................ 128/217, 213, 221, 260

[56] References Cited

U.S. PATENT DOCUMENTS

| | | | |
|---|---|---|---|
| 2,659,369 | 11/1953 | Lipman | 128/217 |
| 2,761,446 | 9/1956 | Reed | 128/217 |
| 3,774,607 | 11/1973 | Schmitz | 128/217 |
| 4,077,406 | 3/1978 | Sandhage et al. | 128/217 |
| 4,105,030 | 8/1978 | Kercso | 128/217 |

Primary Examiner—John D. Yasko
Attorney, Agent, or Firm—James C. Nemmers; Haven E. Simmons

[57] ABSTRACT

An implant gun for depositing pellets or the like subcutaneously. The gun includes a hollow needle through which a number of pellets are dispensed from a cartridge that is positioned either inside the needle or in an ante-chamber. The action of the gun is such that the pellets are gently deposited in the tissue as the needle is withdrawn from the cavity formed in the tissue at the time the needle was inserted. This technique practically eliminates any breaking of the fragile pellets and reduces the trauma of their insertion into the tissue. The implant gun also includes a unique ram activating mechanism that frees one of the hands of the operator so that the implanting procedure can be conducted without assistance. The implant gun is also easily adapted for use in implanting single items other than pellets, such as identification tags for animals.

15 Claims, 12 Drawing Figures

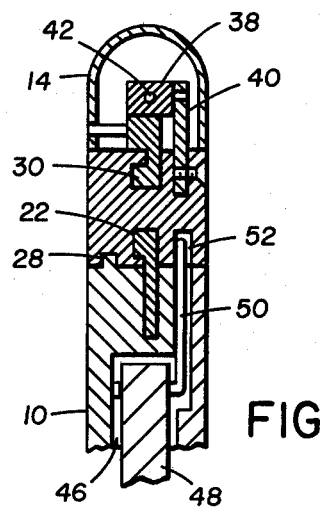
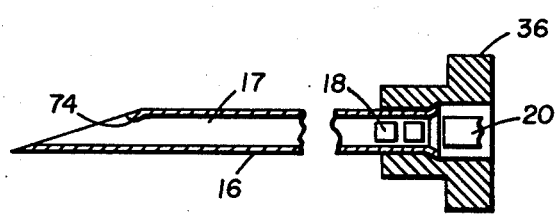
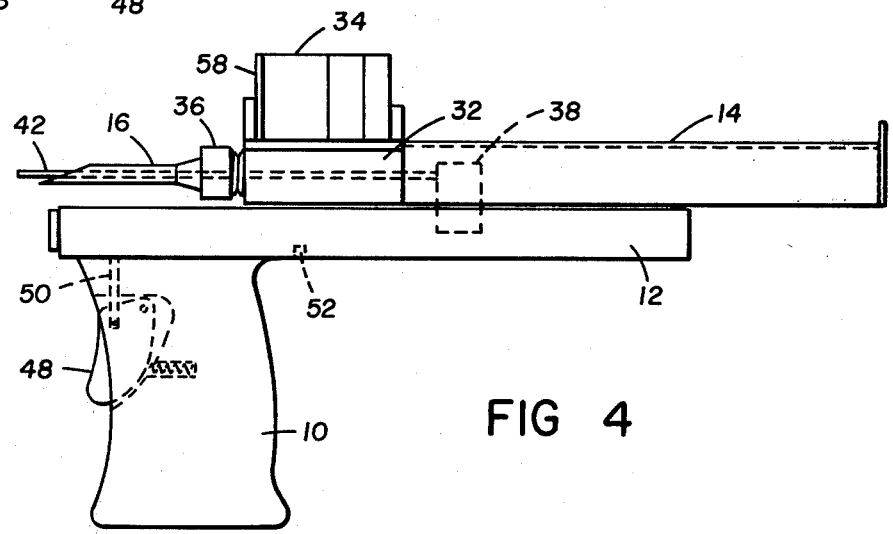
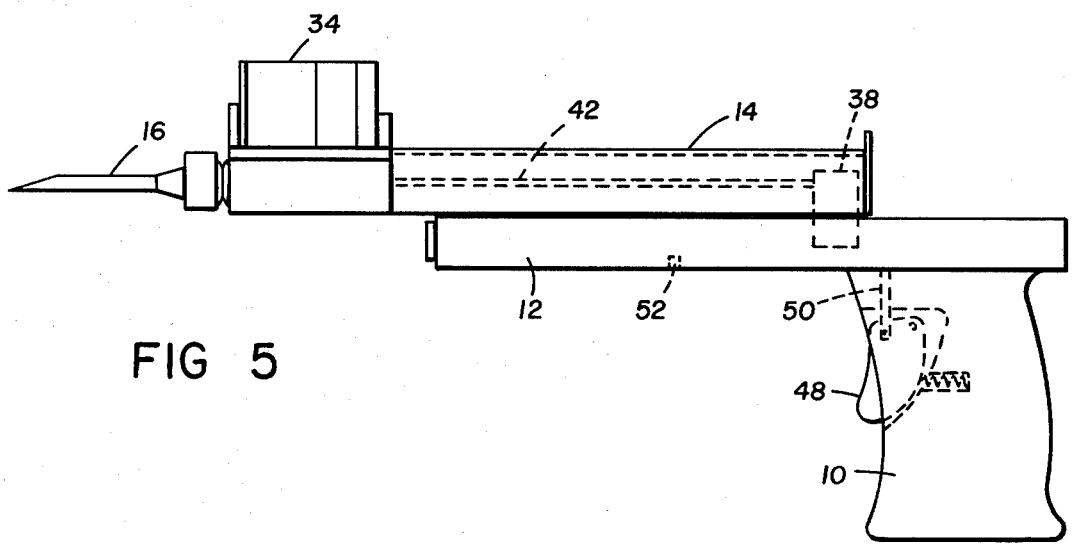

IMPLANT GUN

BACKGROUND OF THE INVENTION

The invention relates to a pellet implant gun especially suitable for use in implanting growth, anabolic or other medicinal pellets under the skin of domestic animals. Use of subcutaneously implanted growth materials is now a common practice in cattle and lamb feedlots, particularly since the feeding of diethyl stilbesterol is a controversial procedure. These growth stimulants are provided by the pharmaceutical manufacturer in pellet form, and for ease in handling and use are commonly packaged with a number of the pellets in a single plastic cartridge. There are known a number of devices, commonly referred to as "implant guns", for implanting these pellets. All of these guns utilize a hollow needle of relatively large diameter which is inserted subcutaneously into the selected implant site of the animal, usually the ear. The prior art implant guns, however, commonly utilize a ram that pushes the pellets out of the cartridge which has been positioned inside of the hollow needle. If enough force is utilized to force the pellets from the end of the needle and into the tissue at the implant site, they often will break. If this occurs, the implanting sometimes must be repeated since all of the pellets will not be inserted under the skin of the animal. Also, if a pellet breaks after it is inserted under the skin, it will be absorbed into the animal's system at a rate that is not desirable and which can sometimes cause adverse side effects on the animal. There is, therefore, a need for an implant gun that will eliminate or greatly minimize the possibility of the pellets being broken at the time they are inserted at the implant site.

Also, there is being developed a variety of means for identifying animals in a manner other than the traditional branding. In large feedlots, it may be desirable for different purposes to place identifying marks on the animals. With the large number of animals in some of the feedlots, checking the identification of the animals can be a very time-consuming process. Therefore, animals are sometimes tagged with special tags which can be detected by means other than visually. It is possible that future developments may permit the implanting of identification means that can be detected electronically so that massive identification of animals can be conducted very rapidly. There is, therefore, a developing need for an implant gun that can also implant metal identification tags for this purpose.

Although the technology has not yet advanced to the point where mass implanting of medicinal pellets in humans is practical, the future use of implant materials in human medicine for birth control, allergy treatment, long-term inoculation, etc. is not inconceivable. Therefore, a need could develop for a suitable implant gun for use in human medicine. If developed for use in human medicine, an implant gun would have to be one which would use as small a needle as possible, handle fragile pellets, and be capable of use with a minimum of trauma to the patient.

SUMMARY OF THE INVENTION

The implant gun disclosed herein provides a device that is clearly suitable for use in the implanting of all types of growth and medicinal pellets under the skin of domestic animals. The basic design of the implant gun of the present invention is also easily adaptable for the implanting of identification tags or other single itemed implants in addition to the implanting of pellets packaged in cartridges. The basic design also is easily adaptable for use in human medicine. The present invention achieves the foregoing by providing an implant gun in which the pellets are not forced into the tissue, but rather as the needle is withdrawn the pellets are gently placed in the cavity formed by the needle at the time it was initially inserted into the tissue. Thus, very little force is applied to the pellets since the only force applied is that necessary to push the pellets out of the cartridge in which they are packaged. The basic design also utilizes an actuating mechanism that is smooth in operation and which permits the gun to be operated with one hand during the implanting step.

The designs of the present invention also allow the use of either a cylinder or a clip for holding a plurality of cartridges or other items to be implanted. Thus, the cylinder or clip can be used for either cartridges or identification tags.

The foregoing features of the invention will become evident from the description of the preferred embodiments of the invention contained hereinafter.

BRIEF DESCRIPTION OF THE DRAWINGS

FIG. 3 is a sectional view taken along the line 3—3 of FIG. 1 and showing the ram activating mechanism;

FIG. 4 is a side elevational view showing the implant gun with the needle retracted so as to place the pellets in the tissue at the implant site;

FIG. 5 is a side elevational view similar to FIG. 4 but showing the implant gun with the components in position for reloading;

FIG. 9 is an enlarged sectional view of a modified needle which holds the cartridge in an antechamber.

DESCRIPTION OF THE PREFERRED EMBODIMENT OF THE INVENTION

Figure 1:
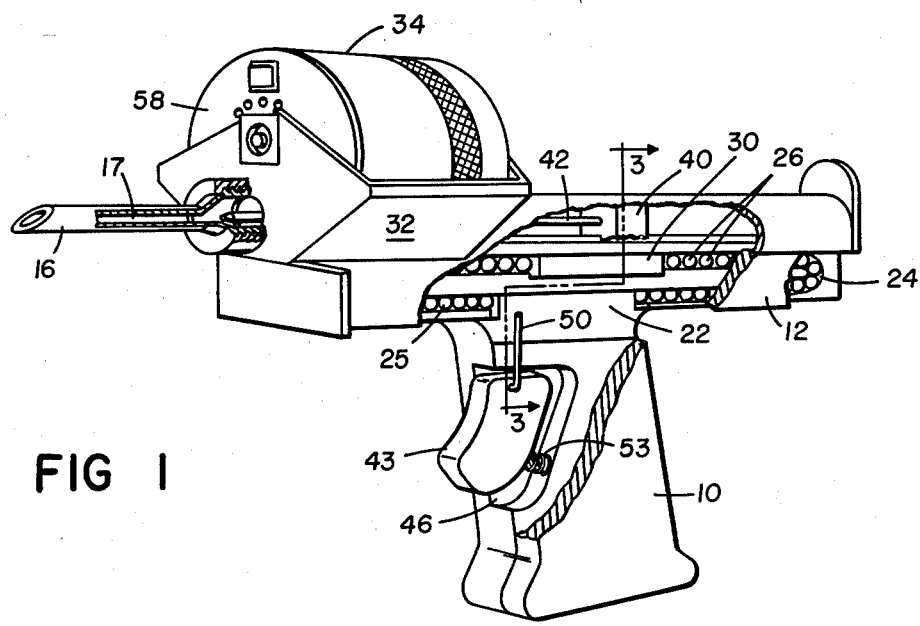
FIG. 1 is a perspective view of an implant gun constructed according to the principles of the invention with the gun partially broken away to show details of the activating mechanism.

Referring now to the drawings and particularly to FIG. 1, there is shown an embodiment of an implant gun constructed according to the principles of the invention. The implant gun has several major components, including a grip or handle 10 that is slidably connected in the manner hereinafter described to an intermediate member 12 which in turn is slidably connected to a main body 14. A hollow needle 16 having a chamber 17 is removably secured to the front end of the main body or carrier 14, and pellets 18 are dispensed through the front of the needle 16 to be implanted in the manner described hereinafter. As is well known, the pellets 18 are of the type packaged in a cylindrical shaped cartridge 20, each cartridge having an annular lip 19 at one end. (See FIG. 1A.)

Extending upwardly at the top of handle 10 is a lower guide member 22 that extends through a longitudinal recess and into an endless path 24 containing a plurality of freely rollable, spherical-shaped bearings 26. The path 24 extends generally longitudinally inside of and from end-to-end of the intermediate member 12. The path 24 is of a cross-sectional shape corresponding to the cross-sectional shape of the upper portion of lower guide member 22 thereby allowing member 22 to move relative to intermediate member 12. The handle 10 also contains an upwardly extending projection 28 that extends into a corresponding longitudinally extending groove in the lower surface of the intermediate member 12, projection 28 serving to guide the handle 10 and intermediate member 12 as they slide longitudinally relative to each other. Because the path 24 curves upwardly and around at each end of the intermediate member 12, the lower guide member 22 also serves as a stop to limit relative movement of the handle 10 with respect to the intermediate member 12. Lower guide 22 also serves to prevent separation of the handle 10 from the intermediate member 12 as these two components move relative to one another in a longitudinal direction from end to end of the intermediate member 12.

The main body 14 is hollow and has extending downwardly therefrom an upper guide member 30 that extends through a longitudinal recess and into the upper portion of the endless path 24 formed in the intermediate member 12. Upper guide member 30 serves to guide the slidable relative movement between intermediate member 12 and main body 14 and also prevents them from becoming separated thereby limiting their relative movement to longitudinal slidable movement.

As best seen in FIG. 1, the sides of the main body 14 flare upwardly and outwardly to form a saddle 32 which provides a chamber into which there is received a cartridge containing cylinder 34. As previously described, the implant needle 16 is affixed to the forward end of the main body 14 and is held in place by a retaining nut 36 so that the needle can be removed and replaced. The chamber 17 of needle 16 is aligned with the hollow chamber formed by the saddle 32, and as will be described hereinafter will be in alignment with one of the cartridge receiving chambers in the cylinder 34.

Figure 2:
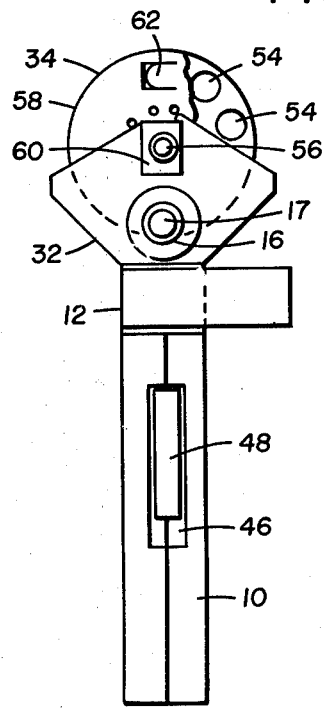
FIG. 2 is a front view of the implant gun of FIG. 1 with parts broken away to show details of the cylinder for holding the cartridges.

As best seen in FIGS. 1 and 2, a ram 38 is affixed to the intermediate member 12 by means of a connecting member 40. Ram 38 is slidably movable on top of the upper guide member 30 which is affixed to and movable with the main body 14. Ram 38 has affixed to it and extending forwardly an operating rod 42 the free or forward end of which extends through a guide opening in a guide member 44 (see FIG. 4) affixed to the main body 14 just rearwardly of the chamber formed by the saddle 32. Thus, since ram 38 and operating rod 42 are connected to the intermediate member 12, relative movement will be produced between rod 42 and the main body 14 which, as more fully described hereinafter, causes the rod 42 to pass through the chamber formed by saddle 32 and into the chamber 17 of needle 16.

In order to control relative movement between the handle 10 and intermediate member 12 and the main body 14 and intermediate member 12, the forward edge of handle 10 has a recess 46 into which there is received a pivotally mounted trigger 48. Trigger 48 has a locking pin 50 pivotally connected to it and extending upwardly to handle 10 and into a recess 52 formed in the bottom surface of intermediate member 12. This is best seen in FIG. 3 and is not shown in FIG. 1 since the portion of the intermediate member 12 shown in FIG. 1 has been broken away to show the interior of the ram actuating mechanism. Trigger 48 is biased into a locking position by means of a spring 53.

Figure 1A:
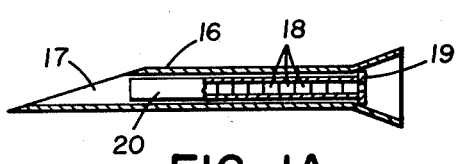
FIG. 1A is a longitudinal sectional view of an implant needle showing a pellet-cartridge in place (partly in section)

With reference to FIGS. 1, 4 and 5, the operation of the implant gun will now be described. FIG. 1 illustrates the gun in a position ready for insertion of needle 16 into the area of the animal in which the implant is to be made. Normally at this point, a cartridge 20 containing the pellets 18 would be positioned inside of the chamber 17 of needle 16. This is not shown in FIG. 1 but is shown in FIG. 1A. Note however from FIG. 1 that in this position the forward end of rod 42 lies inside of the needle and inside of the rear of the cartridge 20. Also, when the components of the gun are in the relative positions shown in FIG. 1, the locking pin 50 would extend into the locking recess 52 in the bottom edge of the intermediate member 12. Thus in this position, the handle 10 cannot move relative to intermediate member 12, nor can the intermediate member 12 move relative to the main body 14 because the upper guide member 30 cannot move in the path 24 being held in place by the spherical-shaped bearings 26. With these components thus locked, the needle is inserted into the implant site of the animal. After insertion into the animal, the trigger 48 is pulled thus pivoting the forward upper end of the trigger downwardly and withdrawing the locking pin 50 from the locking recess 52 in the intermediate member 12. At the same time that the trigger 48 is pulled, the handle 10 is pushed forward toward the animal. As the handle 10 is pushed forwardly, the lower guide member 22 moves the bearings 26 through the endless path 24, and bearings 26 in turn force the upper guide member 30 rearwardly thus carrying with it the main body 14. However, since the rod 42 is connected to the intermediate member 12, the rod 42 remains stationary. Implanting of pellets 18 is accomplished because the rod 42 is holding them in the cavity formed when the needle 16 was inserted, and the needle 16 is withdrawn from the cavity as the main body 14 moves rearwardly when the handle 10 is moved forwardly. Thus, rod 42 remains stationary holding the pellets 18 in the cavity as the needle 16 is withdrawn. FIG. 4 illustrates the relative positions of the components when the handle 10 is pushed to its forward most position. In this position, the rod 42 now extends completely through the chamber 17 in the needle 16 since the needle 16 has been completely withdrawn from the cavity formed at the implant site. The pellets 18 of course are held in the cavity by the rod 42. Thus, the pellets 18 are not forced into the implant site but rather are gently held in the cavity formed at the time the needle is inserted. This is an extremely important aspect of the invention since the pellets 18 are fragile and can be broken if the pellets were pushed into the implant site. With applicant's invention, the cavity is created in the implant site by insertion of the needle 16. There is only the initial trauma of insertion of the needle after which the pellets are merely held in the cavity as the needle 16 is withdrawn. This technique completely eliminates breaking of the fragile pellets and eliminates any additional trauma caused by an attempted forcing of the pellets 18 further into the tissue beyond the cavity formed by insertion of the needle.

Moreover, as is evident from the description of the operation of the implant gun, the procedure can be performed using only one hand. Those skilled in the art will appreciate the convenience and sometimes necessity of having a free hand during the implanting procedure.

FIG. 5 of the drawing illustrates the relative position of the components of the implant gun in a position ready for reloading of an additional cartridge into the needle 16. After the handle 10 has been moved to its forward-most position thus withdrawing the needle 16 (this position is shown in FIG. 4), the gun is removed from the implant site. By grasping the main body 14 with one hand and pulling the handle 10 rearwardly while holding the trigger 48 so that the locking pin 50 does not engage in the locking recess 52, the position of the rod 42 relative to the main body 14 will be such that the rod is completely withdrawn from the chamber formed by saddle 32. This position is shown in FIG. 5. Because the cartridges 20 are normally formed of a somewhat pliable plastic material, the diameter of the rod 42 is preferably made slightly larger than the opening in the rim 19 of the cartridge 20. Thus, as the handle 10 is moved rearwardly forcing the main body 14 forwardly while the rod 42 is stationary, the cartridge 20 will be withdrawn from the needle and into the empty chamber 54 (FIG. 2) of cylinder 34 from which it was originally discharged. As best seen in FIG. 2, cylinder 34 contains a plurality of chambers 54. Cylinder 34 is turnable about a central pivot 56, and the open ends of chambers 54 are normally closed by a front cover member 58 which contains a rectangular shaped positioning member 60 that seats into a correspondingly shaped slot at the top of the saddle 32. Cover 58 contains a single opening (not shown) at the lowermost radial position so that this opening will be in alignment with the chamber 17 in needle 16 when the cylinder 34 is properly seated in the saddle 32. Each of the chambers 54 in the cylinder 34 can be moved into alignment with the discharge opening in cover 58 by rotating cylinder 34 about its pivot 60. If desired, a resilient member 62 can be formed in cover 58 in radial alignment with the chambers 54 so as to hold the cylinder 34 in a selected position with one of the chambers 54 in alignment with the chamber 17 of needle 16.

From the foregoing description of cylinder 34, it will be obvious that a plurality of cartridges 20 can be loaded into chambers 54 of the cylinder 34. The cartridges will be retained in place by means of the cover 58. When the cylinder 34 is properly seated in the saddle 32, cylinder 34 can be rotated so that one of the chambers 54 is in alignment with chamber 17 of needle 16. Of course, this is accomplished when the implant gun is in the loading position shown in FIG. 5. If a cartridge 20 is in the lowermost loading position of cylinder 34, and if the cylinder 34 is properly seated in saddle 32, the operator can grasp handle 10 and move it forwardly. During this step, the trigger should not be pulled so that the locking pin 50 will become engaged in the locking recess 52 as the handle 10 is moved forwardly. This will thus stop forward advancement of handle 10 when the components are in the position shown in FIG. 1. As the handle 10 is moved from the loading position of FIG. 5 to the readied position shown in FIG. 1, relative movement between the main body 14 and rod 42 will force the end of rod 42 into the rear of a cartridge 20 that is in loading position in cylinder 34 and move that cartridge 20 out of cylinder 34 into the chamber 17 of needle 16. The implant gun is then ready for use and for insertion of needle 16 into the implant site. The procedure previously described is then repeated.

Figure 6:
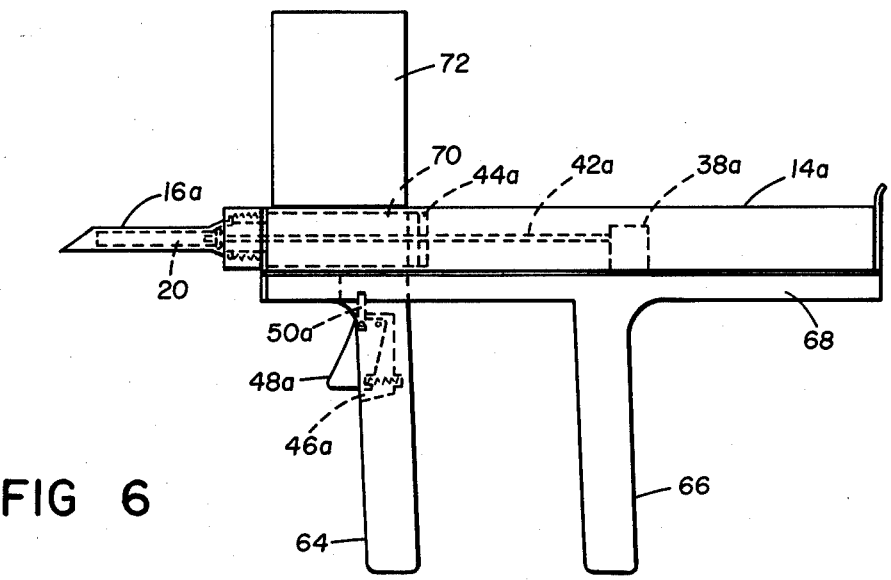
FIG. 6 is a side elevational view showing another embodiment that utilizes a modified ram activating mechanism.
Figure 7:
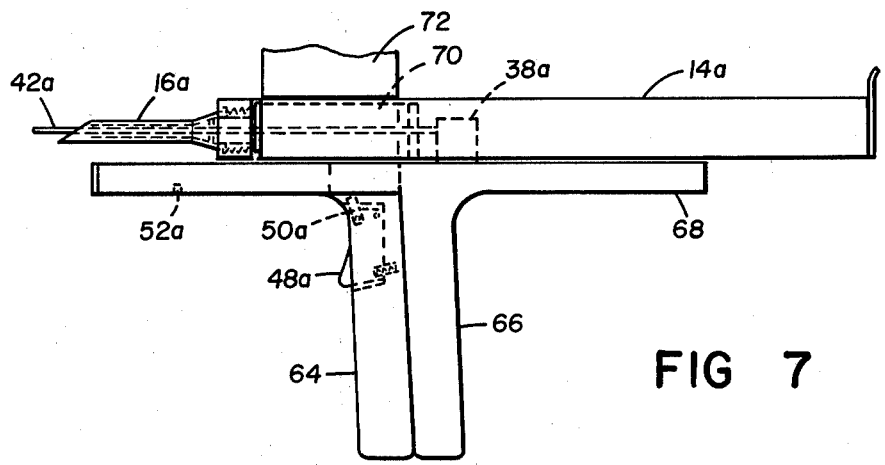
FIG. 7 is a side elevational view of the embodiment of FIG. 6 and showing the implant gun with the needle retracted.
Figure 8:
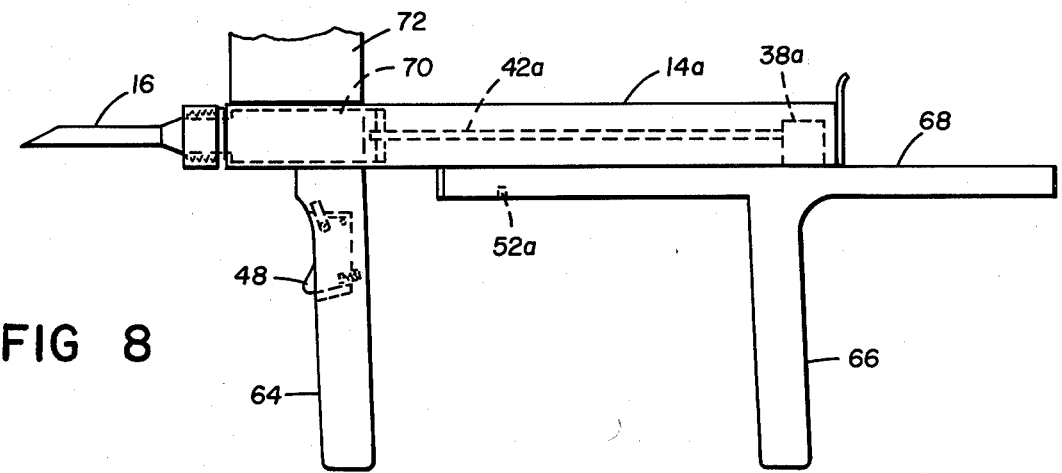
FIG. 8 is a view of the embodiment of FIGS. 6 and 7 but showing the implant gun in a position for reloading.

FIGS. 6, 7 and 8 illustrate a second embodiment of the invention in which the implant gun is somewhat simplified in that the necessity of an intermediate member similar to intermediate member 12 of the first embodiment is eliminated. Components of the second embodiment corresponding to the those of the first embodiment will be referred to with the same reference numeral followed by the letter "a". The implant gun of the second embodiment includes a two piece handle 64 and 66. Handle 66 is formed integrally with or attached to a lower guide member 68 while handle 64 is formed integrally with or attached to the main body 14a. Ram 38a is positioned inside of the main body 14a and is affixed to the lower guide member 68 so as to be movable relative to main body 14a but not movable relative to lower guide member 68.

Handle 64 contains a trigger 48a that is pivotally mounted in a recess 46a in handle 64. Trigger 48a has pivotally connected to its upper forward end a locking pin 50a which is engagable in a locking recess 52a formed in the bottom edge of the lower guide member 68.

Similar to the first embodiment, a rod 42a extends forwardly from the ram 38a with the forward end of rod 42a passing through an opening in a guide member 44a located rearwardly of a chamber 70 formed in the main body 14a rearwardly of the needle 16a. In the embodiment of FIGS. 6-8, there is shown a clip 72 of any suitable design the lower end of which is inserted into chamber 70. Clip 72 replaces the cylinder 34 of the first embodiment. As is obvious to those skilled in the art, clip 72 would hold a plurality of cartridges 20 permitting discharge of them one by one at the lower end of the clip 72 in a manner similar to that of the common automatic hand gun.

The main body member 14a and lower guide member 68 are slidably movable relative to each other and prevent it from separation in any suitable manner such as by using guide members similar to guide members 22 and 30 of the first embodiment. The specific manner in which main body 14a and lower guide member 68 are joined for slidable movement is within the skill of those in the art and further details will therefore not be described.

Operation of the embodiment of the implant gun of FIGS. 6-8 is similar to that of the first embodiment. FIG. 6 illustrates the implant gun loaded and ready for insertion of needle 16a into the implant site. Note that in this position cartridge 20 is positioned in a needle 16a with the end of rod 42a extending inside of the rear of cartridge 20. Also note that the components are locked by reason of engagement of the locking pin 50a in the recess 52a. With one hand on handle 64 and the other hand on handle 66, the trigger 48a is released and the handle 64 pulled rearwardly toward handle 66. At the same time, handle 66 is maintained in its position relative to the implant site. As handle 64 is pulled rearwardly, main body 14a is also moved rearwardly withdrawing needle 16a from the implant site. Since handle 66 is maintained stationary, the rod 42a will hold the pellets 18 in the implant cavity as the needle 16a is withdrawn carrying with it the cartridge 20. After the needle 16a is completely withdrawn, the components will be in the position shown in FIG. 7. In order to prepare the implant gun for the next implant, handles 64 and 66 are moved apart to the position shown in FIG. 8 which moves rod 42a rearwardly to its rearmost position withdrawing the empty cartridge 20 into the chamber 70 from where it can be removed. Another loaded cartridge then will descend downwardly from clip 72, and the handles 64 and 66 moved to the relative position shown in FIG. 6 in which the implant gun is ready for implanting.

FIG. 9 is a sectional view of a needle which has been modified slightly so as to prevent the cartridge 20 from entering into the chamber 17 of the needle 16. Note that all that is required is to modify the diameter of the needle so that the interior diameter of chamber 17 is large enough to receive the pellets but small enough to prevent entry of the cartridge 20. Use of this needle in connection with the implant gun would require a modification of the length of the operating rod 42 and a slight modification to the retaining nut 36. Otherwise, the operation of the implant gun would be identical to that described above with reference to the two preferred embodiments of the invention. The modified needle of FIG. 9 has the advantage of permitting a needle of smaller exterior diameter thus minimizing the trauma of insertion. Preferably, the modified needle of FIG. 9 would also contain a slight indentation 74 at the forward end of the needle inside of chamber 17 to prevent the pellets from inadvertently falling out of the needle once they are inserted into chamber 17 ready for implanting.

There are obviously other modifications which can be made in the preferred embodiments of the invention described herein. For example, the spherical shaped bearings 26 could be replaced by a flexible continuous member or the path could be filled with any flexible means which will move in the path and force the lower guide member 22 and upper guide member 30 to respond as the handle 10 is moved.

Figure 1B:
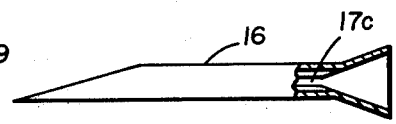
FIG. 1B is a side elevational view, partly in section, of an implant needle for identification tag.
Figure 1C:
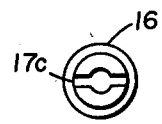
FIG. 1C is an end view of the implant needle of FIG. 1B.

Also, as illustrated in FIGS. 1B and 1C, the implant gun of the invention can be used to implant items in addition to growth stimulants or other medications. FIGS. 1B and 1C illustrate a modification of needle 16 in which the chamber 17c rather than being circular in cross section is rectangular in cross section so as to receive an item such as an electronic identification tag. These and other items can be easily implanted by merely modifying slightly the design of the needle and design of the cartridge 34 or clip 72 holding the item to be implanted.

In addition, it is obvious that there are other means of producing the relative movement between the main components other than an endless path 24 containing flexible means such as those illustrated and described herein. Other mechanical arrangements are within the scope of those skilled in the art in order to produce the relative movement of the components which allows the needle to be withdrawn while the pellets to be implanted are held in the cavity formed at the implant site. These and other modifications and variations are within the skill of those in the art, and it is our intention that all such modifications and revisions as are within the skill of persons ordinarily skilled in the art will be included within the scope of the following claims.

We claim:

1. An implant gun for depositing items such as pellets, identification means and the like subcutaneously, said implant gun comprising a movable carrier, a hollow needle extending from the forward end of said carrier and movable therewith for creating a cavity in the tissue at the implant site when said needle is inserted into said tissue, means for retaining the item to be implanted in position for implanting through said needle, ram means extending into said carrier and engagable with said item, said ram means and said carrier being relatively movable generally forwardly and rearwardly, and operating means for moving said needle and carrier rearwardly while holding said ram means stationary relative to the implant site so as to withdraw said needle from the implant site while holding the item to be implanted in the cavity created at the implant site as said needle is withdrawn.

2. The implant gun of claim 1 in which said carrier includes means located rearwardly of said needle for receiving a holder of a plurality of items to be implanted, said holder being received in said means so as to position an item for implanting through said needle.

3. The implant gun of claim 2 in which said means for receiving a holder of a plurality of items is adapted to receive a revolving cylinder having a plurality of chambers into which the items to be implanted can be inserted.

4. The implant gun of claim 2 in which said means for receiving a holder for a plurality of items is adapted to receive a cartridge having a chamber holding a plurality of items one on top of the other for depositing said items one by one from said chamber.

5. The implant gun of claim 1 in which said operating means includes an intermediate member slidably movable forwardly and rearwardly relative to said main body, and said ram means is affixed to and movable with said intermediate member.

6. The implant gun of claim 5 in which said operating means includes a handle slidably movable forwardly and rearwardly relative to said intermediate member, and connecting means interconnect said main body, intermediate member and handle so that as said handle moves forwardly relative to said intermediate member said main body moves rearwardly relative to said intermediate member, and as said handle moves rearwardly said main body moves forwardly.

7. The implant gun of claim 6 in which said connecting means includes an endless continuous path formed in said intermediate member, a first guide member is affixed to said main body and extends into said path, a second guide member is affixed to said handle and extends into said path, and means in said path interconnecting said first and second guide members so that movement of one of said guide members produces movement of said other guide member in an opposite direction.

8. The implant gun of claim 7 in which said path has an upper portion and a lower portion, and said first guide member extends into said upper portion and said second guide member extends into said lower portion.

9. The implant gun of claim 8 in which said path is filled with a plurality of rollable members freely movable in said path.

10. The implant gun of claim 1 in which said operating means includes a handle slidably movable forwardly and rearwardly relative to said carrier, said ram means being affixed to said handle.

11. The implant gun of claims 1, 5, 6, 7, 8, 9, or 10 in which said operating means includes locking means to selectively prevent relative movement between said carrier and said ram means.

12. The implant gun of claims 1, 2, 3, 4, 5, 6, 7, 8, 9 or 10 in which the item to be implanted is a plurality of pellets contained in a cartridge, and said hollow needle has an interior diameter larger than the exterior diameter of said cartridge so as to receive said cartridge inside of said needle while allowing discharge of said pellets from said cartridge and needle.

13. The implant gun of claims 1, 2, 3, 4, 5, 6, 7, 8, 9, or 10 in which the item to be implant is a plurality of individual pellets contained in a cartridge, and said hollow needle has an interior diameter larger than the exterior diameter of said pellets but smaller than the exterior diameter of said cartridge so that said cartridge remains rearwardly of said needle.

14. A method of implanting items subcutaneously, said method comprising: inserting a hollow needle containing the item to be implanted into the tissue at the implant site to create a cavity at said site; and holding said item stationary relative to said cavity while withdrawing said needle from the implant site so that said item remains in said cavity while said needle is withdrawn.

15. The method of claim 14 wherein a plurality of items are contained in said needle and are implanted in said cavity as said needle is withdrawn.

* * * * *